United States Patent [19]

Malette et al.

[11] 4,452,785
[45] Jun. 5, 1984

[54] METHOD FOR THE THERAPEUTIC OCCLUSION OF BLOOD VESSELS

[76] Inventors: William G. Malette, 667 Parkwood La., Omaha, Nebr. 68132; Herbert J. Quigley, Jr., 9511 Mockingbird Dr., Omaha, Nebr. 68127

[21] Appl. No.: 522,492

[22] Filed: Aug. 12, 1983

Related U.S. Application Data

[63] Continuation-in-part of Ser. No. 440,039, Nov. 8, 1982, which is a continuation-in-part of Ser. No. 251,321, Apr. 6, 1981, Pat. No. 4,394,373.

[51] Int. Cl.³ .............................................. A61K 31/70
[52] U.S. Cl. .................................................... 424/180
[58] Field of Search .......................................... 424/180

[56] References Cited

U.S. PATENT DOCUMENTS 3,911,116 10/1975 Balassa ................................ 424/180

OTHER PUBLICATIONS

Keller et al.,—The American Journal of Surgery, vol. 142 (Jul. 1981), pp. 6–13.

Primary Examiner—Sam Rosen
Attorney, Agent, or Firm—Zarley, McKee, Thomte, Voorhees & Sease

[57] ABSTRACT

A method of occluding blood vessels therapeutically is described wherein chitosan is injected directly into the vessel. The chitosan employed in this invention is partially to fully de-acetylated chitin. The chitin is dissolved in solution with distilled water and acetic acid and has a pH of approximately 4.

5 Claims, No Drawings

METHOD FOR THE THERAPEUTIC OCCLUSION OF BLOOD VESSELS

BACKGROUND OF THE INVENTION

This is a continuation-in-part of our co-pending application, Ser. No. 440,039 filed Nov. 8, 1982 which was a continuation-in-part application of Ser. No. 251,321 filed Apr. 6, 1981, now U.S. Pat. No. 4,394,373.

In applicants' earlier application, a method was described for achieving hemostasis, inhibiting fibroplasia and promoting tissue regeneration. Since the filing of the co-pending application, the inventors have discovered that chitosan may be used intravascularly to occlude blood vessels in the treatment of tumors and internal bleeding.

The prior art teaches that sulfated chitosan injected intravascularly is an anticoagluant which promotes the free flow of blood through the vessel and prevents the formation of blood clots. Our discovery, that chitosan injected intravascularly forms an coagulum and stops the flow of blood in the vessel, teaches directly against the prior art.

Science has long sought an easy method to selectively occlude blood vessels during internal hemorrhage or to selectively occlude the blood supply to tumors not accessible to other forms of treatment. The state of the art today involves the intravascular injection of foreign material through small catheters. Such devices as gelatin pledgets, small wire coils, and plastic materials are used. These act as foreign bodies which induce reaction in tissue, and increase the possibility of infection. Since chitosan forms a coagulum in contact with the cellular elements of blood, it has been used to prevent blood loss from the intersticies of vascular grafts. After a period of time the coagulum has disappeared and has been replaced by normal tissue elements. Therefore, liquid chitosan is easily injected into a blood vessel in which it coagulates and blocks the flow of blood down to the capillary level. After a period of time, it is metabolized and disappears.

Therefore, it is a principal object of this invention to describe a method for the therapeutic occlusion of blood vessels by the injection of chitosan intravascularly.

SUMMARY OF THE INVENTION

Blood vessels are therapeutically occluded by the method of this invention by injecting chitosan intravascularly. The chitosan employed in this invention is partially to fully deacetylated chitin. When the chitosan is injected intravascularly, the vessel is occluded which results in the selective death of tissue or hemostasis in the bleeding vessel.

DESCRIPTION OF THE PREFERRED METHOD

The term chitin embraces naturally occuring chitin synthetic chitin as well as poly-N-acetylglucosamine and its epimer poly-N-acetylglactosamine. Suitable sources of chitin include lobsters, shrimp, other crustacea and fungi. Chitosan is a derivative of chitin and the method of preparing chitosan is described in U.S. Pat. No. 3,533,940 and made a part hereof. Chitosan as used herein refers to de-acetylated chitin. Analysis of the chitosan material used herein reveals that many of the acetyls have been removed from chitin leaving a very reacative free amine group (NH2) on the second carbon of the glucosamine monomers. Polyglucosamine used herein is completely de-acetylated chitin which possesses a free amine group on each glucosamine monomer.

The chitosans used in this method are partially depolymerized chitins in the form of polyglucosamine chains linked by Beta 1-4 glycosidic bonds with many to all acetyl groups removed from the number two positions. Molecular weight determinations may be made by the method of Wu and Baugh (Journal of Chromatography 128, pages 87-99 (1976)). The degree of de-acetylation of the chitosan may be determined by the method of Hayes and Davies (Proceedings of the First International Conference on Chitin/Chitosan pages 193-199 (1978). Chitosan with defined physical and chemical properties may be prepared from any natural source of arthropod exoskeletons or fungal cell walls, by controlling the processes of de-acetylation and depolymerization.

The preferred chitosan employed in this method may be purchased from Kypro, Inc. 208 Carlson Building, Bellevue, Washington and identified as "CHITOSAN—High Viscosity". The preferred chitosan employed in this method is a mixture of polymers with a molecular weight span from 10,000 through 2,055,000 and with individual molecules 78-92% deacetylated. In those chitosan batches tested, the most abundant molecular species have molecular weights of 1,487,000 to 1,682,000 and number averages of 129,000 to 322,000 with a dispersity of 5. The product is 78-92% de-acetylated with a mean of 85% exposed free amine groups.

Although the preferred chitosan employed in the experiments set forth herein was purchased from Kypro, Inc., the term "chitosan" is used by several suppliers to denote a product derived by de-acetylating chitin. It is with chitosans purchased from various sources that the experiments herein began.

The methods of preparing the chitosans so that they could be used in the various experiments are described in detail hereinafter with the preferred preparation method and proportions being described.

Chitosans with various sources of origin, states of depolymerization and/or states of de-acetylation were dissolved at a concentration of 2 grams per liter, in sterile distilled water containing the minimum quantity of acetic acid necessary to dissolve the solid material. The preferred hemostatic chitosan solution is prepared by dissolving 2 grams of chitosan in 998.5 milliliters of sterile distilled water and 1.5 milliliters of glacial acetic acid. The mixture is stirred at room temperature for 2 to 3 hours to produce a clear chitosan solution in 0.026 N acetic acid having a pH of 4.1±0.2. Preferably, the solution is stored at 4° C. Lypholized chitosan solution consisting of dry chitosan acetate salt is equally as effective as fresh solutions when reconstituted to the original volume with sterile distilled water.

The chitosan hemostatic solution may be sterilized by filtrration through 2-micron filters; however, the process is slow. Steam autoclaving of chitosan solutions produces a marked decrease in coagulum-forming effectiveness.

The inventors herein have discovered that chitosan from shrimp, two species of crab, and two unknown sources ("chitosan practical grade") formed a hemostatic coagulum when acid solutions of various concentrations were brought into contact with human blood in test tubes or in skin incisions in dogs. Chitosan which was only 45% de-acetylated required up to 1.0 N acid for solution (with some solid residue). Polyglucosamine formed a good coagulum; however, only small quantities were tested. Lower and medium viscosity chitosans were easily dissolved and quickly sterilized by membrane filters; however, stability of the coagulum was proportional to the molecular weight of the most prevalent polymer in the solution.

EXPERIMENTS

The vascular occlusive effectiveness was tested by comparing the injection of chitosan solutions with a standard method in use by the injection of gelatin pledgets (Gelfoam). The left kidneys of 20 to 30 kilogram weight dogs were surgically exposed. The canine kidney has two distinct branches, one to the upper pole and one to the lower pole. These vessels were isolated. Small hypodermic needles were inserted in each branch. Small pledgets of Gelfoam were injected repeatedly into the lower pole artery until a palor of the cortical surface was observed. Two milliliters of the preferred chitosan solution injected into the upper pole artery produced palor of the cortical surface at once. This was repeated in 11 dogs. The kidneys were removed surgically from one dog immediately following the infusions, and from two dogs at each of the following intervals: 1, 3, 7, 14 and 30 days. The kidneys were examined grossly and microscopically. The results in the upper and lower poles were practically identical in each case. Complete occlusion of the vessel branches was seen in the early specimens. Later, tissue infarcts (death of tissue) were seen in each instance.

The advantage of the liquid material over the solid pledgets was obvious. Considerable force was needed to inject the solid material. Exact placement of the solid material was not possible since the pledgets occluded random branches of the artery, thus requiring multiple injections to achieve the desired result. The liquid chitosan flowed easily into all branches of the vessel and coagulated in situ. After thirty days the gelatin pledgets remained as foreign bodies while the chitosan had disappeared. Low viscosity polyglucosamine required 3.2 milliliters to produce palor. High viscosity 45% de-acetylated chitosan required force to inject and produced irregular pale areas. Each product produced an infarct similar to the gelatin pledget control at 30 days.

The conclusions reached from the above experiments are that the injection of liquid chitosan intravascularly: will easily achieve occlusion of the vessel; will result in the selective death of tissue or hemostasis in a bleeding vessel; and will not remain as a foreign body (unlike other means such as wire coils, gelatin pledgets, or plastic materials).

Thus it can be seen that the method of this invention accomplishes its stated objective.

We claim:

1. The method of occluding a blood vessel therapeutically by the intravascular injection of an effective amount of chitosan into the vessel.

2. The method of claim 1 wherein said chitosan comprises partially to fully de-acetylated chitin.

3. The method of claim 1 wherein said chitosan is dissolved in a solution.

4. The method of claim 3 wherein said solution is formed by dissolving a salt of chitosan.

5. The method of claim 1 wherein said chitosan is in solution with distilled water and acetic acid and has a pH of approximately 4.

* * * * *